US008795201B2

(12) United States Patent
Escutia et al.

(10) Patent No.: US 8,795,201 B2
(45) Date of Patent: *Aug. 5, 2014

(54) CATALYSTS FOR BODY FLUID SAMPLE EXTRACTION

(71) Applicant: Intuity Medical, Inc., Sunnyvale, CA (US)

(72) Inventors: Raul Escutia, Sunnyvale, CA (US); Jeffrey L. Emery, Redwood City, CA (US); Craig M. Litherland, Cupertino, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/752,261

(22) Filed: Jan. 28, 2013

(65) Prior Publication Data

US 2013/0144189 A1 Jun. 6, 2013

Related U.S. Application Data

(60) Continuation of application No. 13/197,592, filed on Aug. 3, 2011, now Pat. No. 8,360,993, which is a continuation of application No. 11/941,403, filed on Nov. 16, 2007, now Pat. No. 8,012,104, which is a division of application No. 11/529,613, filed on Sep. 29, 2006, now Pat. No. 8,012,103.

(60) Provisional application No. 60/721,966, filed on Sep. 30, 2005.

(51) Int. Cl.
*A61B 5/151* (2006.01)

(52) U.S. Cl.
USPC ............... 600/583; 606/182; 600/584

(58) Field of Classification Search
USPC .............. 600/573, 576–579, 583, 584; 606/181–183
See application file for complete search history.

(56) References Cited

U.S. PATENT DOCUMENTS

| 842,690 A | 1/1907 | Oswalt |
| D137,874 S | 5/1944 | Partridge |

(Continued)

FOREIGN PATENT DOCUMENTS

| CA | 2 513 465 A1 | 8/2004 |
| DE | 199 22 413 A1 | 11/2000 |

(Continued)

OTHER PUBLICATIONS

Advisory Action mailed on Feb. 2, 2009, for U.S. Appl. No. 11/529,613, filed Sep. 29, 2006, 3 pages.

(Continued)

*Primary Examiner* — Max Hindenburg
*Assistant Examiner* — John Pani
(74) *Attorney, Agent, or Firm* — Morrison & Foerster LLP

(57) ABSTRACT

An arrangement for producing a sample of body fluid from a wound opening created in a skin surface at a sampling site includes at least one skin-penetration member having a first end configured to pierce the surface of the skin, and a inner lumen in communication with the first end; at least one actuator operatively associated with the at least one skin-penetration member; and at least one catalyst device configured to cause perfusion of body fluid at the sampling site; wherein the at least one actuator is configured to locate the at least one skin-penetration member so as to obstruct the wound opening while transporting body fluid through the inner lumen. Associated methods are also described.

10 Claims, 9 Drawing Sheets

(56) References Cited

U.S. PATENT DOCUMENTS

| | | |
|---|---|---|
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,767,415 A | 8/1988 | Duffy |
| 4,774,192 A | 9/1988 | Terminiello et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,846,785 A | 7/1989 | Cassou et al. |
| 4,887,306 A | 12/1989 | Hwang et al. |
| 4,920,977 A | 5/1990 | Haynes |
| 4,930,525 A | 6/1990 | Palestrant |
| 4,935,346 A | 6/1990 | Phillips |
| 4,953,552 A | 9/1990 | De Marzo |
| 4,966,646 A | 10/1990 | Zdeblick |
| 4,995,402 A | 2/1991 | Smith |
| 5,029,583 A | 7/1991 | Meserol |
| 5,049,487 A | 9/1991 | Phillips et al. |
| 5,050,617 A | 9/1991 | Columbus et al. |
| 5,059,394 A | 10/1991 | Phillips et al. |
| 5,077,199 A | 12/1991 | Basagni et al. |
| 5,094,943 A | 3/1992 | Siedel et al. |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Haber et al. |
| 5,218,966 A | 6/1993 | Yamasawa |
| 5,223,219 A | 6/1993 | Subramanian et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,275,159 A | 1/1994 | Griebel |
| 5,278,079 A | 1/1994 | Gubinski et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Mike et al. |
| 5,304,468 A | 4/1994 | Phillips et al. |
| 5,306,623 A | 4/1994 | Kiser et al. |
| 5,308,767 A | 5/1994 | Terashima |
| 5,320,607 A | 6/1994 | Ishibashi |
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,399,316 A | 3/1995 | Yamada |
| 5,401,110 A | 3/1995 | Neeley |
| 5,402,798 A | 4/1995 | Swierczek et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,611,809 A | 3/1997 | Marshall et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,701,181 A | 12/1997 | Boiarski et al. |
| 5,701,910 A | 12/1997 | Powles et al. |
| 5,705,018 A | 1/1998 | Hartley |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |

(56) References Cited

U.S. PATENT DOCUMENTS

| | | |
|---|---|---|
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,891,053 A | 4/1999 | Sesekura |
| 5,893,870 A | 4/1999 | Talen et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,888 B1 | 11/2001 | Wong et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,740,800 B1 | 5/2004 | Cunningham |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| 6,988,996 B2 | 1/2006 | Roe et al. |
| 7,004,928 B2 | 2/2006 | Aceti et al. |
| 7,011,630 B2 | 3/2006 | Desai et al. |

(56) References Cited

U.S. PATENT DOCUMENTS

| | | |
|---|---|---|
| 7,025,774 B2 | 4/2006 | Freeman et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| D551,243 S | 9/2007 | Young |
| 7,270,970 B2 | 9/2007 | Anderson et al. |
| 7,297,151 B2 | 11/2007 | Boecker et al. |
| 7,343,188 B2 | 3/2008 | Sohrab |
| 7,344,507 B2 | 3/2008 | Briggs et al. |
| 7,427,377 B2 | 9/2008 | Zanzucchi et al. |
| D599,373 S | 9/2009 | Kobayashi et al. |
| D601,578 S | 10/2009 | Poulet et al. |
| 7,682,318 B2 | 3/2010 | Alden et al. |
| 7,803,123 B2 | 9/2010 | Perez et al. |
| 7,887,494 B2 | 2/2011 | Emery et al. |
| D642,191 S | 7/2011 | Barnett et al. |
| 2001/0001034 A1 | 5/2001 | Douglas |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0083685 A1 | 5/2003 | Freeman et al. |
| 2003/0083686 A1 | 5/2003 | Freeman et al. |
| 2003/0116596 A1 | 6/2003 | Terasawa |
| 2003/0135166 A1 | 7/2003 | Gonnelli |
| 2003/0135333 A1 | 7/2003 | Aceti et al. |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2004/0010207 A1 | 1/2004 | Flaherty et al. |
| 2004/0030353 A1 | 2/2004 | Schmelzeisen-redeker et al. |
| 2004/0049219 A1 | 3/2004 | Briggs et al. |
| 2004/0059256 A1 | 3/2004 | Perez |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0096959 A1 | 5/2004 | Stiene et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0236251 A1 | 11/2004 | Roe et al. |
| 2004/0238675 A1 | 12/2004 | Banaszkiewicz et al. |
| 2005/0010134 A1 | 1/2005 | Douglas et al. |
| 2005/0015020 A1 | 1/2005 | LeVaughn et al. |
| 2005/0096686 A1 | 5/2005 | Allen |
| 2005/0106713 A1 | 5/2005 | Phan et al. |
| 2005/0159678 A1 | 7/2005 | Taniike et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0117616 A1 | 6/2006 | Jones et al. |
| 2006/0135873 A1 | 6/2006 | Karo et al. |
| 2006/0155317 A1 | 7/2006 | List |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0179404 A1 | 8/2007 | Escutia et al. |
| 2007/0179405 A1 | 8/2007 | Emery et al. |
| 2007/0255181 A1 | 11/2007 | Alvarez-icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0194934 A1 | 8/2008 | Ray et al. |
| 2009/0156923 A1 | 6/2009 | Power et al. |
| 2010/0021948 A1 | 1/2010 | Lipman et al. |
| 2010/0095229 A1 | 4/2010 | Dixon et al. |
| 2010/0185120 A1 | 7/2010 | Sacherer et al. |
| 2012/0166090 A1 | 6/2012 | Lipman et al. |

FOREIGN PATENT DOCUMENTS

| | | |
|---|---|---|
| DE | 103 02-501 A1 | 8/2004 |
| EP | 0 396-016 A2 | 11/1990 |
| EP | 0 396-016 A3 | 11/1990 |
| EP | 0 255-338 A2 | 2/1998 |
| EP | 1 266-607 A2 | 12/2002 |
| EP | 1 266-607 A3 | 12/2002 |
| EP | 1 360-934 A1 | 11/2003 |
| EP | 1 360-934 B1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-318970 A | 12/1998 |
| JP | 2000126161 A | 5/2000 |
| JP | 2000-168754 A | 6/2000 |
| JP | 2000-254111 A | 9/2000 |

(56) References Cited

FOREIGN PATENT DOCUMENTS

| | | |
|---|---|---|
| JP | 2001-159618 A | 6/2001 |
| JP | 2001-305096 A | 10/2001 |
| JP | 2001-330581 A | 11/2001 |
| JP | 2002-502045 A | 1/2002 |
| JP | 2002-514453 A | 5/2002 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2006-512969 A | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-521031 A | 8/2007 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | WO-99/44508 A1 | 9/1999 |
| WO | WO-99/58051 A1 | 11/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-2003/030984 A1 | 4/2003 |
| WO | WO-2003/066128 A2 | 8/2003 |
| WO | WO-2003/066128 A3 | 8/2003 |
| WO | WO-2003/070099 A1 | 8/2003 |
| WO | WO-2003/071940 A1 | 9/2003 |
| WO | WO-2003/071940 C1 | 9/2003 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/018709 A2 | 3/2005 |
| WO | WO-2005/018709 A3 | 3/2005 |
| WO | WO-2005/084546 A2 | 9/2005 |
| WO | WO-2005/084546 A3 | 9/2005 |
| WO | WO-2005/085995 A1 | 9/2005 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |

OTHER PUBLICATIONS

Advisory Action mailed on Apr. 8, 2010, for U.S. Appl. No. 11/529,613, filed Sep. 29, 2006, 3 pages.
Extended European Search Report mailed on Jan. 22, 2013, for EP Application No. 12182900.6, filed on Sep. 29, 2006, 6 pages.
Final Office Action mailed on Jul. 9, 2008, for U.S. Appl. No. 11/529,613, filed Sep. 29, 2006, 19 pages.
Final Office Action mailed on Nov. 23, 2009, for U.S. Appl. No. 11/529,613, filed Sep. 29, 2006, 20 pages.
Final Office Action mailed on Jan. 21, 2011, for U.S. Appl. No. 11/529,613, filed Sep. 29, 2006, 7 pages.
International Search Report mailed on Aug. 16, 2007 for PCT Application No. PCT/US2006/038163, filed on Sep. 29, 2006, 1 page.
Interview Summary mailed on Jan. 13, 2009, for U.S. Appl. No. 11/529,613, filed Sep. 29, 2006, 4 pages.
Interview Summary mailed on Nov. 1, 2010, for U.S. Appl. No. 11/529,613, filed Sep. 29, 2006, 3 pages.
Interview Summary mailed on May 17, 2012, for U.S. Appl. No. 13/197,592, filed Aug. 3, 2011, 3 pages.
Interview Summary mailed on May 17, 2012, for U.S. Appl. No. 13/197,603, filed Aug. 3, 2011, 3 pages.
Interview Summary mailed on Aug. 27, 2012, for U.S. Appl. No. 13/197,592, filed Aug. 3, 2011, 3 pages.
Interview Summary mailed on Aug. 27, 2012, for U.S. Appl. No. 13/197,603, filed Aug. 3, 2011, 3 pages.
Non-Final Office Action mailed on Dec. 12, 2007, for U.S. Appl. No. 11/529,613, filed Sep. 29, 2006, 13 pages.
Non-Final Office Action mailed on Apr. 28, 2009, for U.S. Appl. No. 11/529,613, filed Sep. 29, 2006, 21 pages.
Non-Final Office Action mailed on Jun. 4, 2010, for U.S. Appl. No. 11/529,613, filed Sep. 29, 2006, 23 pages.
Non-Final Office Action mailed on Mar. 23, 2012, for U.S. Appl. No. 13/197,592, filed Aug. 3, 2011, 7 pages.
Non-Final Office Action mailed on Mar. 23, 2012, for U.S. Appl. No. 13/197,603, filed Aug. 3, 2011, 6 pages.
Notice of Allowance mailed on May 3, 2011, for U.S. Appl. No. 11/529,613, filed Sep. 29, 2006, 12 pages.
Request for Continued Examination filed on Feb. 4, 2009, for U.S. Appl. No. 11/529,613, filed Sep. 29, 2006, 2 pages.
Request for Continued Examination filed on Apr. 23, 2010, for U.S. Appl. No. 11/529,613, filed Sep. 29, 2006, 2 pages.
Response to Non-Final Office Action filed on Apr. 11, 2008, for U.S. Appl. No. 11/529,613, filed Sep. 29, 2006, 18 pages.
Response to Non-Final Office Action filed on Jul. 28, 2009, for U.S. Appl. No. 11/529,613, filed Sep. 29, 2006, 27 pages.
Response to Non-Final Office Action filed on Nov. 4, 2010 for U.S. Appl. No. 11/529,613, filed Sep. 29, 2006, 18 pages.
Response to Non-Final Office Action filed on Aug. 23, 2012 for U.S. Appl. No. 13/197,592, filed Aug. 3, 2011, 7 pages.

(56) References Cited

OTHER PUBLICATIONS

Response to Non-Final Office Action filed on Aug. 23, 2012 for U.S. Appl. No. 13/197,603, filed Aug. 3, 2011, 7 pages.
Response to Final Office Action filed on Jan. 9, 2009, for U.S. Appl. No. 11/529,613, filed Sep. 29, 2006, 23 pages.
Response to Final Office Action filed on Mar. 23, 2010, for U.S. Appl. No. 11/529,613, filed Sep. 29, 2006, 25 pages.
Response to Final Office Action filed on Apr. 12, 2011, for U.S. Appl. No. 11/529,613, filed Sep. 29, 2006, 11 pages.
Written Opinion mailed on Aug. 16, 2007 for PCT Application No. PCT/US2006/038163, filed on Sep. 29, 2006, 4 pages.
Ada Consensus Development Panel. (Jan.-Feb. 1987). "Consensus Statement on Self-Monitoring of Blood Glucose," *Diabetes Care* 10(1):95-99.
Ada (Jan. 1994). "Self-Monitoring of Blood Glucose," Consensus Statement *Diabetes Care* 17(1):81-86.
Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.
Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.
Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.
Chase, H.P. et al. (Feb. 2001). "Continuous Subcutaneous Glucose Monitoring in Children with Type 1 Diabetes," *Pediatrics* 107(2):222-226.
Clarke, W.L. et al. (Sep.-Oct. 1987). "Evaluating Clinical Accuracy of Systems for Self-Monitoring of Blood Glucose," *Diabetes Care* 10(5):622-628.
Cox, D.J. et al. (Jun. 1997). "Understanding Error Grid Analysis," *Diabetes Care* 20(6):911-912.
D'Arrigo, T.D. (Mar. 2000). "GlucoWatch Monitor Poised for Approval," *Diabetes Forecast*, 53(3):43-44.
Johnson, R.N. et al. (Jan. 1998). "Accuracy of Devices Used for Self-Monitoring of Blood Glucose," *Annals of Clinical Biochemistry* 35(1):68-74.
Johnson, R.N. et al. (Jan. 1999). "Analytical Error of Home Glucose Monitors: A Comparison of 18 Systems," *Annals of Clinical Biochemistry* 36(1):72-79.
Johnson, R.N. et al. (2001). "Error Detection and Measurement in Glucose Monitors," *Clinica Chimica Acta* 307:61-67.
Lee, S-C. (Jun. 1999). "Light Scattering by Closely Spaced Parallel Cylinders Embedded in a Finite Dielectric Slab," *Journal of the Optical Society of America A* 16(6):1350-1361.
McNichols, R.J. et al. (Jan. 2000). "Optical Glucose Sensing in Biological Fluids: An Overview," *Journal of Biomedical Optics*, 5(1):5-16.

Medline Plus. (Jun. 17, 2008). , Medical Encyclopedia, Monitor Blood Glucose-Series: Part 1-4, 6 pages.
Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Trinder, P. (1969). "Determination of Glucose in Blood Using Glucose Oxidase with an Alternate Oxygen Acceptor," *Annals of Clinical Biochemistry* 6:24-28.
Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.
Feldman, B. et al. (2000). "FreeStyle$^{TM}$: A Small-Volume Electrochemical Glucose Sensor for Home Blood Glucose Testing," *Diabetes Technology and Therapeutics*, 2(2):221-229.
Kumetrix, Inc. (Dec. 1999). "Painless Blood Glucose Monitoring, Courtesy of the Mosquito," *Start-Up* pp. 27-28.
Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.
McGarraugh, G. et al. (2001). "Physiological Influences on Off-Finger Glucose Testing," *Diabetes Technology & Therapeutics* 3(3):367-376.
Neeley, W.E. et al. (1981). "An Instrument for Digital Matrix Photometry," *Clinical Chemistry* 27(10):1665-1668.
Neeley, W.E. (1983). "Reflectance Digital Matrix Photometry," *Clinical Chemistry* 29(6):1038-1041.
Neeley, W.E. (1983). "Multilayer Film Analysis for Glucose in 1- μL Samples of Plasma," *Clinical Chemistry* 29(12):2103-2105.
Neeley, W.E. (1988). "A Reflectance Photometer with a Square Photodiode Array Detector for Use on Multilayer Dry-Film Slides," *Clinical Chemistry* 34(11):2367-2370.
Otto, E. et al. (2000). "An Intelligent Diabetes Software Prototype: Predicting Blood Glucose Levels and Recommending Regimen Changes," *Diabetes Technology and Therapeutics* 2(4):569-576.
Smart, W.H. et al. (2000). "The Use of Silicon Microfabrication Technology in Painless Glucose Monitoring," *Diabetes Technology & Therapeutics* 2(4):549-559.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Yum, S. I. et al. (Nov. 1, 1999). "Capillary Blood Sampling for Self-Monitoring of Blood Glucose," *Diabetes Technology & Therapeutics*, 1(1):29-37.

CATALYSTS FOR BODY FLUID SAMPLE EXTRACTION

CROSS-REFERENCE TO RELATED APPLICATIONS

The present application is a Continuation of and claims priority to U.S. patent application Ser. No. 13/197,592, filed Aug. 3, 2011, which issued as U.S. Pat. No. 8,360,993 on Jan. 29, 2013, which is a Continuation of, and claims priority pursuant to 35 U.S.C. §120, to, U.S. patent application Ser. No. 11/941,403, filed Nov. 16, 2007, which issued as U.S. Pat. No. 8,012,104 on Sep. 6, 2011, which is a Divisional of, and claims priority under 35 U.S.C. §120 to, U.S. patent application Ser. No. 11/529,613, filed Sep. 29, 2006, which issued as U.S. Pat. No. 8,012,103 on Sep. 6, 2011, which claims priority to 35 U.S.C. §119 to U.S. Patent Application No. 60/721,966 filed Sep. 30, 2005. The entire contents of each of these applications are hereby incorporated by reference in this application.

FIELD

The present invention relates to devices, arrangements and methods involving body fluid sampling with the assistance of a catalyst. In certain embodiments, the present invention is directed to integrated monitoring and body fluid sampling and monitoring devices and methods that permit both digital and alternative-site body fluid sampling and analysis.

BACKGROUND

In the discussion that follows, reference is made to certain structures and/or methods. However, the following references should not be construed as an admission that these structures and/or methods constitute prior art. Applicants expressly reserve the right to demonstrate that such structures and/or methods do not qualify as prior art.

According to the American Diabetes Association, diabetes is the fifth-deadliest disease in the United States and kills more than 213,000 people a year, the total economic cost of diabetes in 2002 was estimated at over $132 billion dollars. One out of every 10 health care dollars is spent on diabetes and its complications. The risk of developing type I juvenile diabetes is higher than virtually all other chronic childhood diseases. Since 1987 the death rate due to diabetes has increased by 45 percent, while the death rates due to heart disease, stroke, and cancer have declined.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, and often confusing and complicated for the user. The systems require significant user intervention.

Technology development in the field of self-monitoring of blood glucose has placed the burden of acquiring sufficient blood for conducting a test on the user of the technology. Historically, diabetics have been taught to lance their finger tips to produce blood for conducting the test. Ironically, the fingers are not only one of the most sensitive body parts to pain, but they also are among the areas of skin that are most highly perfused with blood. Earlier versions of consumer-oriented self-monitoring products usually required many microliters of blood, and the finger tips provided a reasonably convenient area to lance that would be most likely to produce the required volume of blood.

More recently, some self-monitoring systems offer the option to the user to test at alternate sites such as the palm, forearm, or thigh. While these sites are generally known to be significantly less sensitive to the pain associated with lancing, the adoption of alternate site testing has been limited for at least four reasons: (1) only a few meter products have been approved by the FDA for testing at alternate sites at this time; (2) many testers do not know that they can use their device at the alternate sites; (3) many testers find it relatively difficult to express sufficient blood at the alternate sites to perform a test; (4) data published in medical literature on some of the meters shows that there may be a distinct difference between glucose levels measured at alternate sites relative to the finger, particularly when glucose levels are falling and/or the subject may be hypoglycemic. Consequently, there is a perception by the medical community that there may be an increased risk for delayed or improper treatment by the diabetic if they act only on the basis of glucose levels measured from alternate sites. Thus, the finger lancing site remains the most frequently used test site by far.

Lancing devices and the lancets themselves have also evolved somewhat over the past few decades. Some lancing mechanisms may produce relatively less pain by either (1) projecting the lancet in and out of the skin in a more straight path and thus reducing stimulation of percutaneous nerves which provide the pain stimulus; and (2) offering depth control in the lancing device so that the user may balance the expression of sufficient blood against the level of pain. Furthermore, lancet manufacturers offer a variety of lancet sizes, lengths, and tip bevel patterns with some companies claiming that their lancet is less painful than others.

What remains clear is that the most testers, when lancing at the finger, often must put down the lancing device and apply pressure near the finger tip in order to produce sufficient blood for the test strip in the meter. Many instructions for use with conventional meter systems specifically prescribe that the user perform this "milking" process because without it, many will not spontaneously produce the required volume. Applicants have observed this phenomenon in the use of commonly available commercial sampling and meter systems. In a recent study, when a trained professional lanced the finger tips of 16 volunteer diabetic subjects at the maximum depth setting on commercially available device under controlled conditions, only 15% of lanced sites spontaneously produced sufficient blood for the meter to accurately measure glucose levels.

Attempts have been made in the past to take steps toward automation of the testing process at alternate sites. Specifically, the Sof-Tact® System offered by Medisense in the early 2000s had the capability to test automatically at alternate sites without any user intervention, but only after each lancet and test strip had been manually loaded into the device. This meter is no longer available on the market.

A device similar to the Soft-Tact® device is disclosed in U.S. Patent Application Publication No. 2004/0138588 A1. This device attempts to integrate all the functions required to complete a glucose test into one device. This device however still requires the user to load a lancet and a test strip prior to each individual testing event, and fails to describe a catalyst (i.e.—mechanism to stimulate or enhance expression of blood from the lanced wound site) that ensures that a sufficient sample is expressed from the wound.

The device is described in U.S. Patent Application Publication No. 2005/0010134 A1, and U.S. Pat. No. 6,793,633 B2 uses a spring, or motor driven mechanism, to apply pressure around the target wound area. From the description it appears that the user must insert a new lancet and test strip assembly for each test.

Another disadvantage with conventional arrangements such as the ones referenced above is that they involve complex and sometimes ineffective mechanisms for transferring blood or body fluid from the wound to a remote location for analysis. For example, many conventional arrangements and techniques utilize a solid lancet for creating a wound in the surface of the skin. After piercing the skin the lancet is retracted and a separate member, such as a tube, is positioned to transfer the blood or body fluid. Alternatively, an absorbent test strip is moved into position, manually or in an automated fashion, so that it absorbs the sample of blood or body fluid from the wound site. These arrangements and techniques are overly complex, and clearly rely upon the precise positioning of the tube or test strip to transfer the sample of blood or body fluid. When seeking to automate the sampling process, this precise positioning requires rather complex mechanical arrangements and controls that must operate under close tolerances. Such complex systems and arrangements are either costly, unreliable, or both.

Thus, conventional sampling devices and methods are overly reliant upon user intervention, such as milking, in order to consistently express a sufficient quantity of blood from the wound site, or are overly complex and/or lack reliability.

Moreover, while many diabetics continue to test their blood glucose levels with blood from the finger, testing at the alternate sites offers the advantage of significantly less pain when lancing the palm, forearm, etc. Thus, it would be advantageous to have an automatic and fully integrated meter constructed for sampling and/or testing at either the finger and the alternate sites.

SUMMARY OF THE INVENTION

According to the present invention, there are provided body fluid sampling and monitoring devices and methods that may address one or more of the shortcomings noted above associated with conventional systems and devices. According to the present invention, there may also be provided improved body fluid sampling and monitoring devices and methods that enable both digital and alternative-site body fluid sampling without significant user intervention.

As used herein "digital" means fingers or toes. "Digital body fluid" means expression of body fluid from a wound created on the fingers or toes, and encompasses lancing sites on the dorsal or palm side of the distal finger tips.

As used herein "alternate site" means a location on the body other than the digits, for example, the palm, forearm or thigh. "Alternate-site body fluid sampling" means expression of body fluid from the lancing site on a surface of the body other than the fingers or toes, and encompasses lancing sites on the palm, forearm, and thigh.

As used herein, "body fluid" encompasses whole blood, intestinal fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid.

As used herein, the term "obstructed opening" means that the needle or skin piercing element is not retracted prior to extracting the body fluid from the wound created thereby. Thus, for example, the portion of the opening or wound on or just below the surface of the skin is at least partially obstructed by the skin piercing member or needle which will be located at the wound opening entrance on or just below the surface of the skin upon extraction of body fluid. This aspect of the present invention is believed to run counter to the conventional wisdom in the art. See, for example, U.S. Pat. No. 6,063,039.

According to one aspect, the present invention is directed to an arrangement for producing a sample of body fluid from a wound opening created in a skin surface at a sampling site, the arrangement comprising: at least one skin-penetration member having a first end configured to pierce the surface of the skin, and a inner lumen in communication with the first end; at least one actuator operatively associated with the at least one skin-penetration member; and at least one catalyst device configured to enhance perfusion of body fluid at the sampling site;

wherein the at least one actuator is configured to locate the at least one skin-penetration member so as to obstruct the wound opening while transporting body fluid through the inner lumen.

According to another aspect, the present invention is directed to a method of sampling body fluid from a wound opening created in a skin surface at a sampling site, the method comprising: automatically or manually initiating a testing sequence; applying a catalyst to the sampling site; actuating a skin-piercing member so as to drive the member into the surface of the skin thereby creating the wound opening; allowing the at least one skin-penetration member to obstruct the wound opening; and transporting body fluid through an inner lumen of the skin-penetration member; wherein the catalyst is applied to the sampling site at one or more of the following times: prior to actuating the skin-piercing member, during actuation of the skin-piercing member, or after actuating the skin-penetration member.

BRIEF DESCRIPTION OF THE DRAWING FIGURES

The following description of preferred embodiments can be read in connection with the accompanying drawings in which like numerals designate like elements and in which.

DETAILED DESCRIPTION

Figure 1:
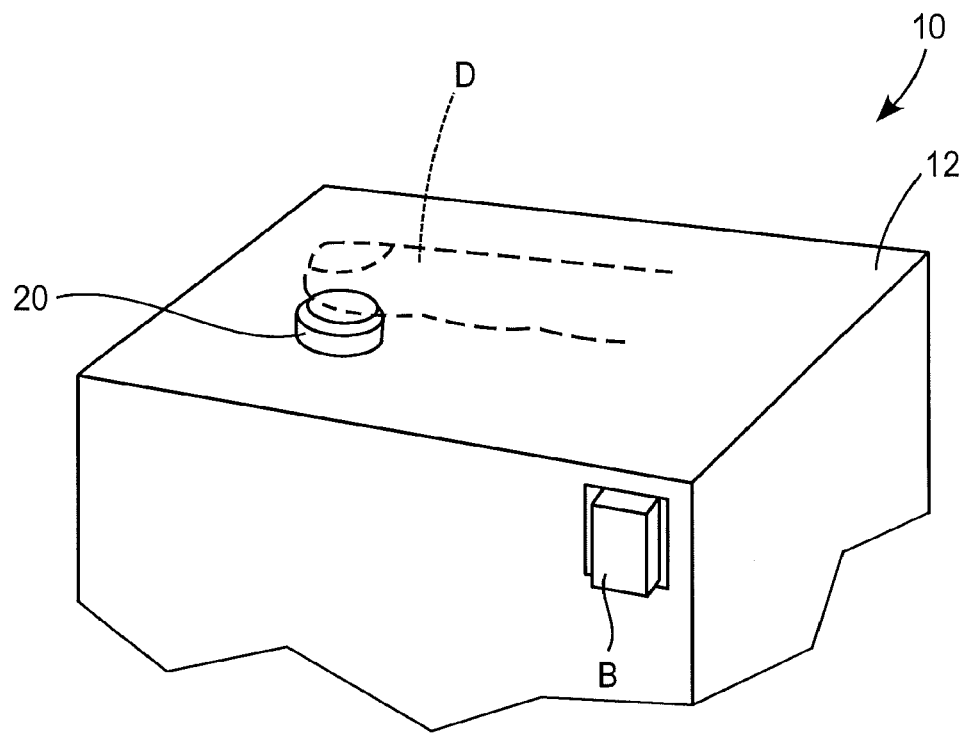
FIG. 1 is a partial perspective view of an arrangement constructed according to the present invention.
Figure 2:
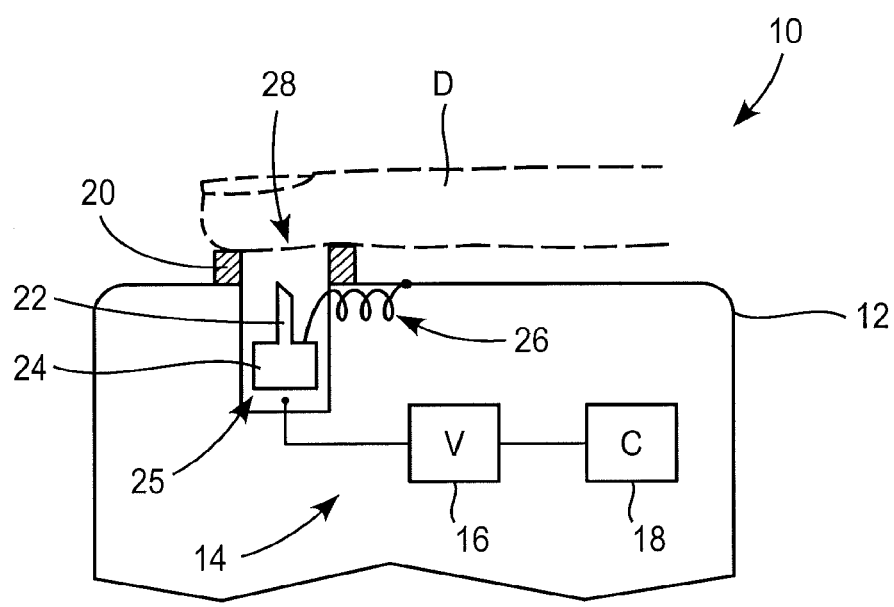
FIG. 2 is a partial cut away side view of the arrangement of FIG. 1.
Figure 3:
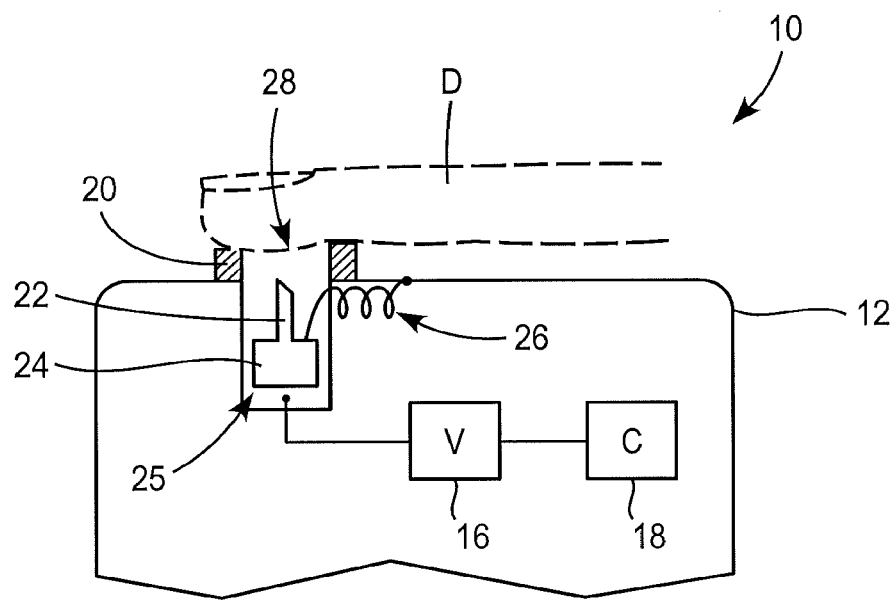
FIG. 3 is a partial cut away side view of the arrangement of FIG. 1, with an activated catalyst.

According to a first aspect of the present invention, there are provided arrangements and techniques for reliably expressing body fluid from a digit or from an alternate site. For example, according to the present invention, arrangements and techniques are provided which consistently and reliably express an amount of body fluid that is sufficient to perform an analysis to quantify the amount of an analyte (e.g., glucose, bilirubin, alcohol, controlled substances, toxins, hormones, proteins, etc.) contained therein.

One embodiment of an arrangement 10 of the type described above is illustrated in FIGS. 1-4. As illustrated therein, the arrangement 10 may include a housing 12. The housing 12 may have any suitable shape or configuration, and is not limited to the shape and configuration illustrated. The housing 12 can be constructed of any suitable material. For example, the housing 12 may be constructed of a polymeric or metallic material.

The arrangement 10 may further include a catalyst to assist in the sample acquisition process by enhancing perfusion of blood or body fluid at a sampling site. At least one of several catalysts may be utilized or included in the arrangement of the present invention. Possible catalysts include, lancing velocity, heat, pressure, vacuum, vibration, and topical drugs (which induce vasodilatation and increases the blood or body fluid available at the lancing site). These catalysts may be applied before, during, after lancing, or in combination with some or all three to facilitate expression of sufficient quantity of body fluid for determination of the concentration of an analyte contained therein (e.g., glucose).

Lancing velocity refers to the speed at which the skin piercing member is driven. Velocities ranging from ~0-22 m/s are possible. Both pain and blood production may increase as velocity increases. Attempts to balance pain and blood have led to a preferred range of about 3-20 m/s, 3-10 m/s, or 10-12 m/s.

Pressure is another possible catalyst. Footprint contact pressure can be varied by a number of possible techniques. One such technique is to vary the size of the opening of the footprint. Another form of pressure catalyst can take the form of a pressure-applying member that circumferentially surrounds and squeezes the digit or other body part from which a sample is to be acquired. One illustrative example of this form of catalyst is a pressure-applying cuff-like member of the type described in U.S. patent application Ser. No. 11/510,784, entitled BODY FLUID MONITORING AND SAMPLING DEVICES AND METHODS, the entire content of which is incorporated herein by reference. The above-described pressure catalyst can be utilized alone, or in combination with other catalysts such as vacuum pressure.

Heat is another optional catalyst. Increasing heat, thereby increasing the skin temperature at the wound site, increases blood production. Possible implementations of heat include IR lights, or resistive elements to heat the skin.

Another catalyst is vacuum pressure. According to certain embodiments, a light vacuum (e.g., 3-8 in. Hg) is applied to the wound site before, during, and/or after lancing. Several embodiments for applying vacuum to the wound site are contemplated. One embodiment uses a motor driven pump to apply vacuum. Alternative embodiments include using individually packaged vacuum chambers to apply vacuum, or using a rigid syringe like mechanism to apply vacuum. Other systems use motor driven pumps and syringes.

According to the principles of the present invention, one or more of the above-described catalysts can be used in combination with each other, either concurrently or sequentially.

In certain specific embodiments of the arrangement 10, a catalyst device 14 can be included which comprises a member or combination of members for applying pressure to a surface of the skin S disposed at a location which is proximate to an area from which a sample of body fluid is to be expressed (i.e., sampling site 28). The catalyst device 14 may cause the area of the skin from which the sample of body fluid is to be expressed to become perfused with blood and/or body fluid. This effect facilitates expression of body fluid from a wound opening 30. According to the illustrated embodiment, the catalyst device 14 comprises a member or combination of members, such as the illustrated pump 16 and related controller 18.

The arrangement 10 further comprises a footprint 20 which is attached to the housing 12. According to the illustrated embodiment, a digit D is placed on the footprint 20 at the sampling site. However, it should be understood that the footprint may also be applied to the surface of the skin at an alternate site. The footprint 20 has a central opening and may optionally have an annular in shape. However, the footprint is not limited to this shape or configuration. Numerous shapes or configurations may satisfy the function of providing a footprint around the site from which body fluid is to be expressed. The footprint can have an opening of any suitable diameter or major dimension 21. According to an illustrative example, the diameter or major dimension is at least about 3-8 mm. According to certain embodiments, the footprint 20 is constructed from a material which facilitates the formation of a seal between the digit D and the footprint 20. For example, suitable materials for this purpose include a relatively soft elastomeric material, such as a silicone rubber.

The arrangement 10 further includes at least one skin penetration member 22. The at least one skin penetration member 22 can take any suitable form. For example, the at least one skin penetration member can comprise a solid lancet or a hollow needle. Conventional arrangements often require separate mechanisms for drawing a sample of blood to the surface of the skin and for transporting the sample to a reaction chamber. The device of the present invention can use a skin-piercing element in the form of a hollow needle to both create and transport the sample, thereby greatly simplifying and improving the effectiveness of the arrangement 10. According to one optional embodiment, the skin-penetration member(s) 22 can be in the form of a so-called "microneedle." As the name implies, microneedles are characterizable by their relatively small outer diameters. For example, a microneedle, as the term is utilized herein, may encompass a skin-penetration member having an outside diameter which is on the order of 40-200 μm. The inside diameter can vary, for example, having an inside diameter on the order of 25-160 μm. Needles are also characterizable in the art by reference to the "gage." By way of illustration, and consistent with the above description, microneedles having a gage ranging from 26-36 are clearly comprehended by the present invention. Certain advantages may be gleaned from the use of such microneedles as the skin-penetration member. In particular, due to their small size, the size of the wound left upon entry into the skin is relatively small, thereby minimizing the pain associated with such needle insertions and allowing for a quicker healing process. However, the present invention is certainly not limited to the use of such microneedles. Thus, for example, according to one possible alternative embodiment, the skin penetration member(s) comprise hollow needles having a gage of about 20-25, or comprising hollow needles having an inner diameter of about 0.007 inches and an outer diameter of about 0.020 inches.

The at least one skin-penetration member 22 can be formed of any suitable material, such as metal, plastic, glass, etc. Optionally, the at least one skin penetration member can be mounted to a hub 24. In further alternative embodiments, the hub 24 may contain an assay pad 34 comprising a reagent that changes color upon reaction with a target analyte, as known per se to those skilled in the art. As illustrated, for example, in FIG. 2, the skin-penetration member 22 and hub 24 may be located within a chamber 25. The chamber 25 is in communication with pump 16 so that vacuum pressure can be applied within the chamber 25. The arrangement 10 can comprise a plurality of skin penetration members 22. According to certain embodiments, the plurality of skin penetration members 22 can be provided in the form of a replaceable cartridge. The at least one skin penetration member 22, and/or the hub 24 are attached to an actuation element 26. The actuation element 26 can take any suitable form. For example, the actuation element 26 may comprise a mechanical, electrical or pneumatic element. According to the illustrated embodiment, the actuation element 26 is in the form of a mechanical spring, more specifically, in the form of a torsional spring.

Figure 4:
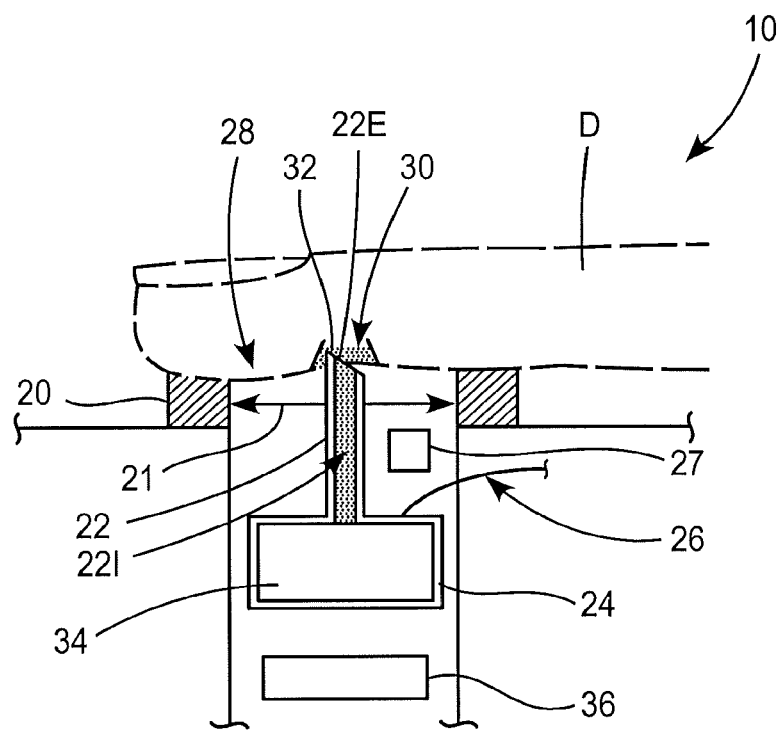
FIG. 4 is a partial cut away magnified side view of the arrangement of FIG. 1, with an activated catalyst and illustrating a mechanism of body fluid collection and transport according to the present invention.

According to certain embodiments of the present invention, the catalyst device 14 operates in an automatic or semi-automatic manner. For example, a user may place the footprint 20 over a surface of the skin on a digit D, or at an alternate site. When the user is ready to produce a sample of body fluid, the button B is pressed. This can initiate a programmed sequence of events in the device including actuation of the catalyst device 14, thereby applying vacuum pressure to the skin an area proximate the tip region of digit D or alternate sampling site (FIG. 3) for a predetermined period of time. The skin-penetration member 22 can then be driven into the skin (FIG. 4). At a predetermined time, the catalyst device 14 is deactivated. This mode of operation can be characterized as "semi-automatic" in that sequence of events must be manually initiated by the user via pressing the button B.

According to one alternative, the mode of operation can be fully automatic. For example, the user places a tip region of digit D on the footprint 20, or places the footprint over an alternate site. The arrangement 10 can be provided with one or more sensors 27 that detect and verify that the footprint is properly located and ready for the sampling procedure to begin. Once this state has been sensed, the device automatically activates the catalyst 14 which is applied to the skin at the sampling site 28 (FIG. 3) for a predetermined period of time. Subsequently, the at least one skin penetration member 22 is driven into the skin (FIG. 4). At a subsequent predetermined time, the catalyst device 14 is deactivated. The catalyst device can be deactivated before, during or after the skin-piercing member is driven into the skin.

The arrangement 10 can form at least part of a device which functions only to sample body fluid. For example, the arrangement 10 can be used to express body fluid from the skin in the form of a drop of blood which pools on the surface of the skin of the user. This drop of blood can then be transferred to another separate device which then transports and/or analyzes the sample for a target analyte. Alternatively, the arrangement 10 may express a sample of body fluid from the skin, and then transport the sample to a location which can then be accessed for further analysis by a separate device. For instance, the sample body fluid can be transported to a reagent-containing pad 34, also contained within the arrangement 10. The sample then reacts with the reagent to produce a detectable spot or signal. The reagent pad can then be analyzed by a separate meter using photochemical, electrochemical, or other suitable techniques known per se to those skilled in the art. The reagent pad can remain within the arrangement 10 during the aforementioned analysis. According to an alternative embodiment, the reagent pad 34 can be analyzed by a detector 36 that forms part of the arrangement 10. Alternatively, the reagent pad can be removed from the arrangement 10 and inserted into a separate device, such as an electrochemical or photometric meter.

As illustrated, for example, in FIG. 4, according to this optional aspect of the present invention a skin-piercing member 22 in the form of a needle having a first end 22e configured to pierce the skin and an inner lumen 22l is driven into the skin to create a wound opening 30 therein for producing a sample of body fluid 32, preferably blood. The needle is not retracted right away, instead it is allowed to dwell and obstruct the opening 30 created in the surface of the skin. Blood or body fluid 32 is then extracted and flows through the inner lumen 22l of the needle, and is eventually transported to a site within the arrangement 10 for further analysis. The blood or body fluid 32 is drawn though the inner lumen by any suitable mechanism, such as capillary action, vacuum, or a combination of both. The needle 22 may be caused to dwell at the desired location via any of the mechanisms described herein. The skin-piercing member 22 is eventually retracted (see, e.g., FIG. 2). It has been surprisingly observed that an adequate sample volume can be extracted by the above-described arrangement/technique, especially when utilizing a vacuum catalyst. This arrangement and technique is advantageous in that a skin piercing member 22 may be used for wound creation and sample transport. Complex mechanisms and arrangements for repositioning a transport member or assay pad to a location that does not obstruct the opening can be avoided. Other advantages of obstructed opening sampling is realizing a reduction in the required sample volume, and improving the reliability of obtaining an adequate sample. When the needle is located so as to obstruct the wound opening, the end of the needle is closer to the source of body fluid, thus smaller drops of sample are more likely to reach the inner lumen of the needle and be successfully transported as the needle rests on or in the skin. By contrast, when the needle is withdrawn away from the surface of the skin, as in conventional arrangements and techniques, the droplet of blood or body fluid must be significantly larger/taller to reach the end of the needle and lumen, thereby elevating the risk that an insufficient sample is obtained.

Figure 5:
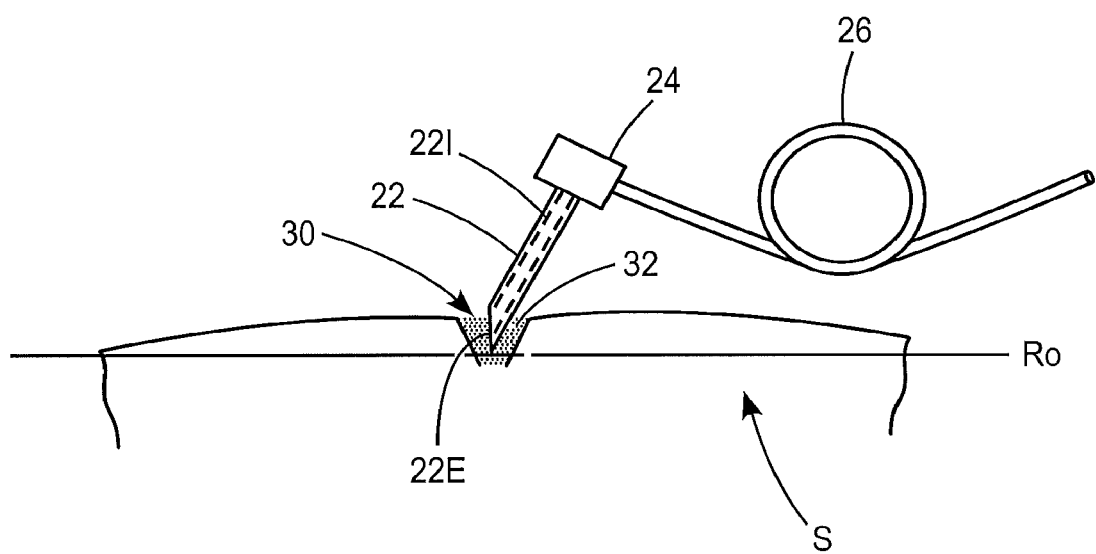
FIG. 5 is a perspective view of a portion of an arrangement, including an actuator, constructed according to the present invention.
Figure 6:
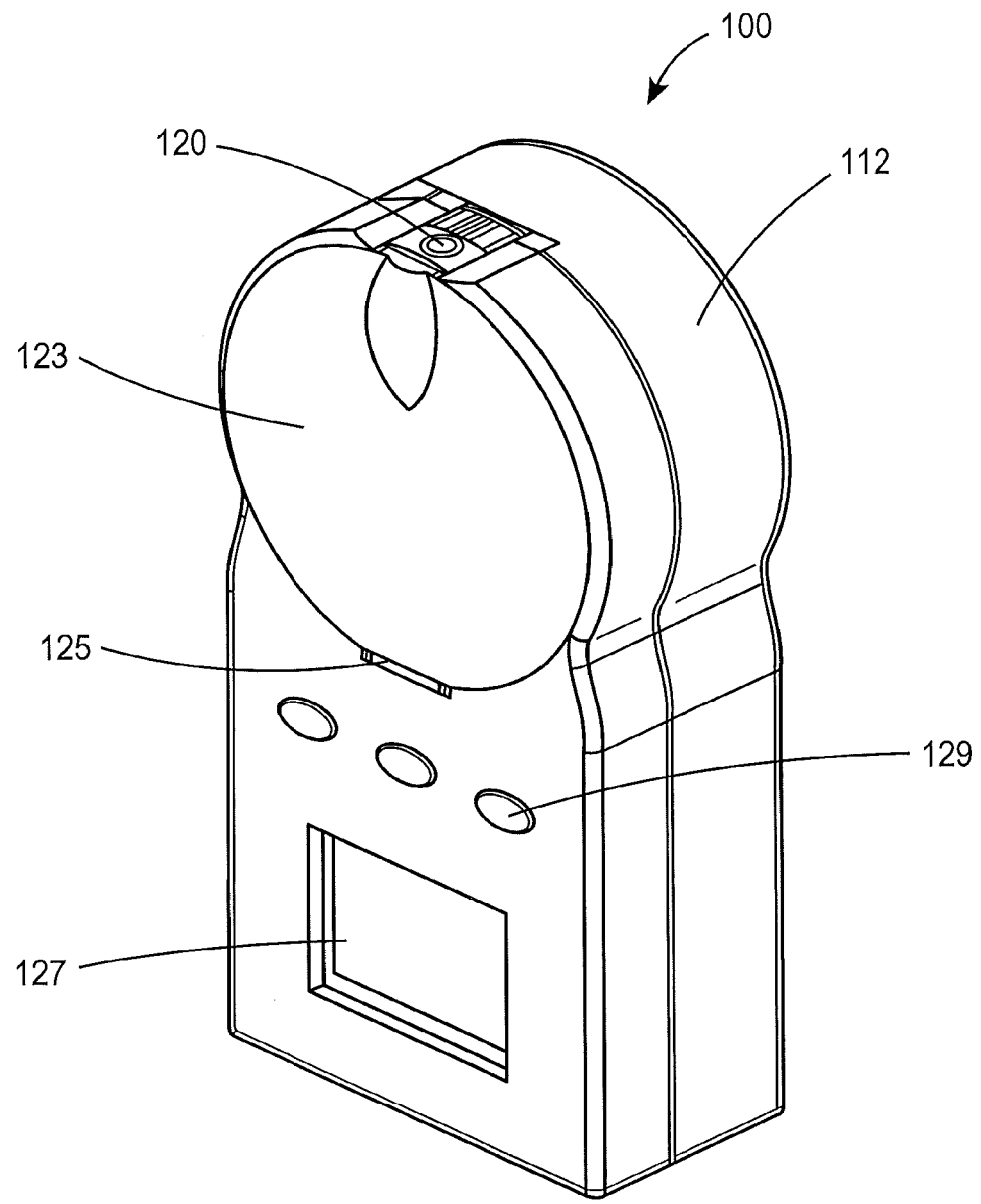
FIG. 6 is a perspective view of an integrated device formed according to one embodiment of the present invention.

As illustrated in FIG. 5, each individual skin-piercing element 22 is provided with its own actuation element or torsional spring 26. The torsional spring elements 26 may be provided to the user in a pre-cocked position. The acceleration path of the skin-piercing element or needle 22 may begin up to 180 degrees from the angle of impact with the skin S of the user. According to one beneficial aspect, the pivot point of the torsional spring elements can be provided as close as possible to the plane lying on the surface of the skin S in order to ensure that the skin piercing element 22 strikes the skin at an angle which is as close to 90 degrees as possible. The torsional spring element 26 can act as a guide for the skin-piercing element or needle 22 to that locates the tip 22e thereof so as to obstruct the wound opening 30 so as to draw the blood 32 into the lumen 22 l of the needle. In this regard, the torsional spring element 26 may be designed such that its neutral position Ro will locate the needle so as to obstruct the wound opening 30 created by the skin piercing operation.

Another advantage of this optional aspect of the present invention is that the torsional spring elements 26 do not require a positive stop to limit the penetration depth of the skin-piercing element 22. It has been observed that elimination of a hard stop may provide certain beneficial effects. Namely, it has been observed that devices that include a hard stop experience a shock and resulting vibration and/or stirring action when the stop is impacted. It is theorized that this motion may increase the observable wound and/or the perceived pain associated with sampling. According to this embodiment, the depth of penetration of the skin-penetrating member 22 is determined by a number of factors, including the design of the sharp, the actuation force and the skin's resistance to penetration at the chosen sampling site. The lack of a positive stop has not been observed as increasing pain in clinical studies.

An exemplary body fluid sampling method or technique which may be used in conjunction with any of the above-described arrangements, but is not necessarily limited thereto, is described as follows.

A footprint is placed over a sampling site located on a digit or at an alternate site. The footprint has an opening therein which defines the sampling site. A sequence of events is then initiated. The events can be initiated manually, for example, by pressing a button or other triggering mechanism. Alternatively, the events can be automatically triggered, for example, through the use of sensors which determine when the footprint has been property positioned over a sampling site on the surface of the skin. A catalyst is then applied to the sampling site. The catalyst can comprise one or more of lancing velocity, heat, pressure, vacuum, vibration, topical drugs, or combinations thereof. These catalysts can be applied concurrently or sequentially relative to one another. According to one embodiment, a catalyst in the form of vacuum pressure is applied to the sampling site via a suitable mechanism, such as a pump capable of creating vacuum pressure. The catalyst can be applied for a set period of time, and then removed or terminated. For example, the catalyst can be removed before, during, or after penetration of the skin. Next, at least one skin penetration member is actuated or driven into the surface of the skin. The skin penetration member can take any suitable form, such as a solid lancet or hollow needle (e.g., a microneedle). According to one embodiment, at least one skin penetration member comprises a hollow needle having a first end configured to pierce the surface of the skin, and an inner lumen. The at least one skin penetration member can be actuated via any suitable mechanism, such as a mechanical spring. According to one optional embodiment, the actuating mechanism comprises a torsional spring. The at least skin penetration member is caused to dwell at or below the surface of the skin in the vicinity of the wound opening in order to obstruct the same. The skin penetration member can be caused to dwell at this location via any suitable mechanism. According to one embodiment, the actuator is provided in the form of a torsional spring having a resting position which can be utilized to cause the first end of the at least one skin penetration member to obstruct the wound opening subsequent to piercing the surface of the skin. During the period of time in which the at least one skin penetration member is caused to dwell at the wound opening, body fluid is transported away from the wound site via a suitable mechanism. According to one embodiment, the body fluid, or blood, is transported via the inner lumen of a hollow skin-penetration member via capillary action, vacuum, or a combination of both. According to one optional embodiment of the present invention, a mechanism can be provided which estimates the acquired sample volume, and compares this measured sample volume with a target sample volume. The information acquired by this analysis can be used to control the catalyst such that it is automatically removed once the target sample volume has been acquired. Any suitable mechanism can be utilized to analyze the acquired sample volume. For example, the body fluid can be transported to an assay pad which contains a chemical reagent impregnated therein. Upon exposure to the body fluid, a target analyte contained therein causes a chemical reaction producing a color change in the assay pad. This color change can in turn be detected by a suitable detection element. One such detection element utilizes colorimetric optical analysis of the assay pad. More specifically, an array of such detection elements can be provided along a longitudinal length of the assay pad. The number of detection elements contained along the length of the assay pad that detect the presence of the sample can be correlated to the acquired sample volume. For example, the further the sample volume travels along the length of the assay pad the greater the acquired sample volume. Once it has been determined that a target sample volume has been acquired, the catalyst can then be terminated. This can be accomplished by the use of a controller in signal communication with a pump. The controller operates based on signals derived from the analysis of the sample volume in the manner described above. Some advantages of monitoring volume to actively control the application of the catalyst include reduction in expression of excess blood or body fluid thereby reducing mess, preventing damage to skin (bruising, etc) due to prolonged catalyst application, and reduction in power consumption.

According to a further optional aspect of the present invention, the above-described arrangements and methods can form at least part of an integrated device or integrated meter. As previously noted, as used herein, the term "integrated device" or "integrated meter" means a device or meter that includes all components necessary to perform sampling of the body fluid, transport of the body fluid, quantification of an analyte, and display of the amount of analyte contained in the sample of body fluid. Thus, according to the principles of the present invention, an integrated device or meter can comprise one or more, or any combination, of the features previously described herein. According to further aspects of the present invention, and integrated meter or device can comprise components and/or features in addition to those specifically described herein.

An exemplary integrated meter is illustrated in detail in FIGS. 6-10. As illustrated therein, the integrated meter 100 generally comprises a housing 112 and a catalyst device 114 (e.g., FIG. 10). The catalyst device 114 may take any suitable form and can comprise any of the previously described alternative catalyst devices. The integrated meter 100 may further comprise a footprint 120 of the type previously described. A door 123 can be provided on the housing 112. The door 123 is connected via a hinge 125 to the housing 112. As described in further detail below, the door 123 can be opened to reveal a cartridge 131 containing a plurality of skin-piercing elements 122. In the illustrated embodiment, the integrated meter 100 further includes a display 127 for communicating the results of the analysis on the sample body fluid for the presence and/or concentration of an analyte contained therein. The integrated meter 100 may further include one or more buttons 129 which can be pressed by the user to engage various functions and interfaces of the integrated meter 100.

Figure 7:
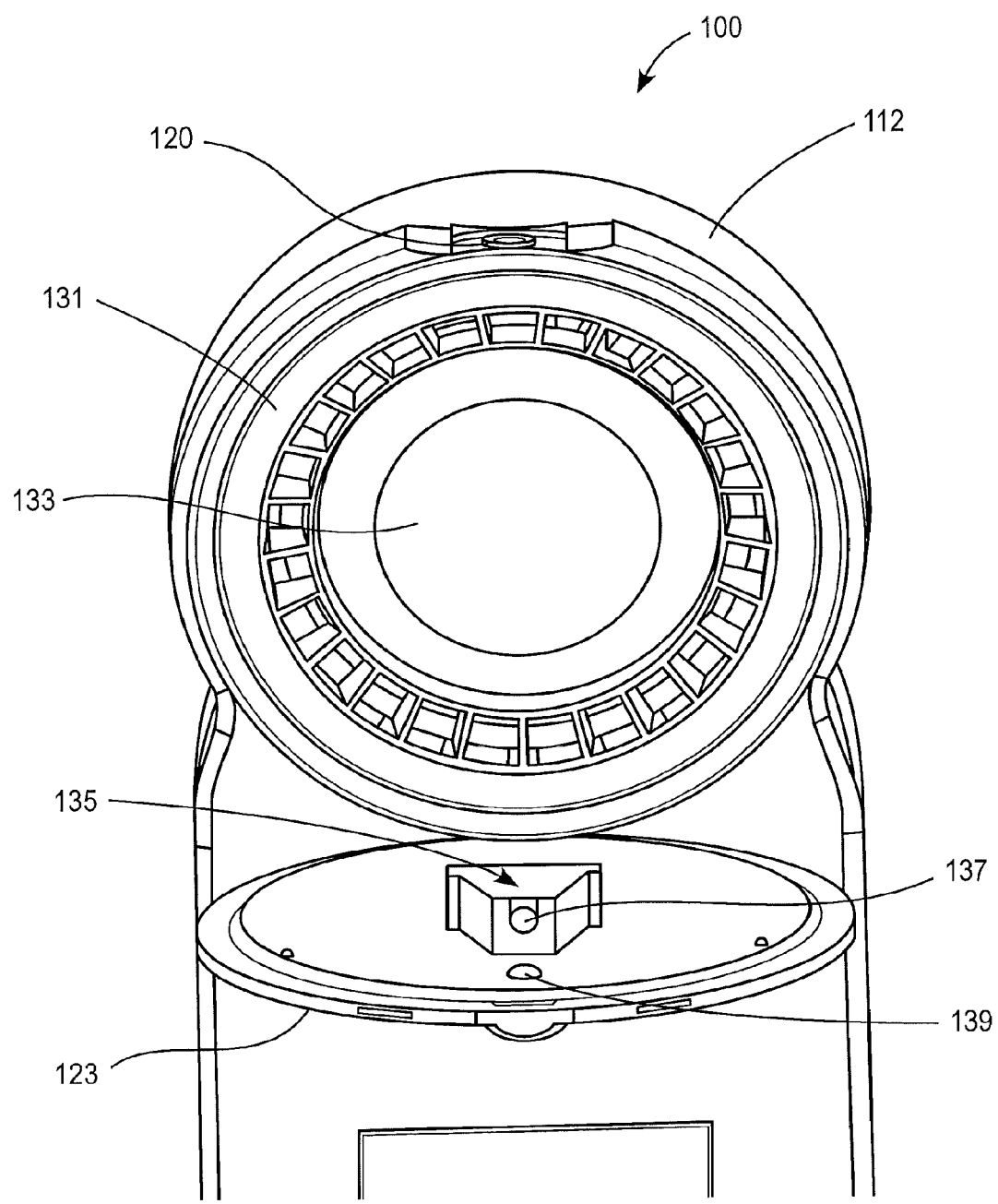
FIG. 7 is a partial side view of the integrated device of FIG. 6.

FIG. 7 is an illustration of the integrated meter 100 with the door 123 opened to reveal further details of the interior components of the exemplary integrated meter 100. As illustrated therein, the housing 112 contains a cartridge 131 therein. In the illustrated embodiment, the cartridge 131 is circular and contains a plurality of skin-piercing elements as further described herein. The cartridge 131 is mounted about a hub 133 and is rotatable. Thus, upon sampling a skin-piercing element 22 is driven through an opening in the housing in registry with the footprint 120 and pierces the skin of the user. Once the test has been completed, the cartridge 131 can be rotated such that an unused skin-piercing element now comes into registry with the opening in the housing and the corresponding opening in the footprint 120 in preparation for the next sampling event. It should be understood that the present invention is not limited to the illustrated circular cartridge having the particular configuration depicted in the drawing figures. To the contrary, a number of alternative cartridge configurations are possible, such as a slidable linear or polygonal configuration (not shown). Also illustrated in FIG. 7 is the presence of a light source 139 disposed on the back of the door 123. The light source 139 can take any suitable form, such as a light emitting diode. It should be understood that alternative light sources may also be utilized. The function of the light source 139 will be described in further detail below.

Figure 8:
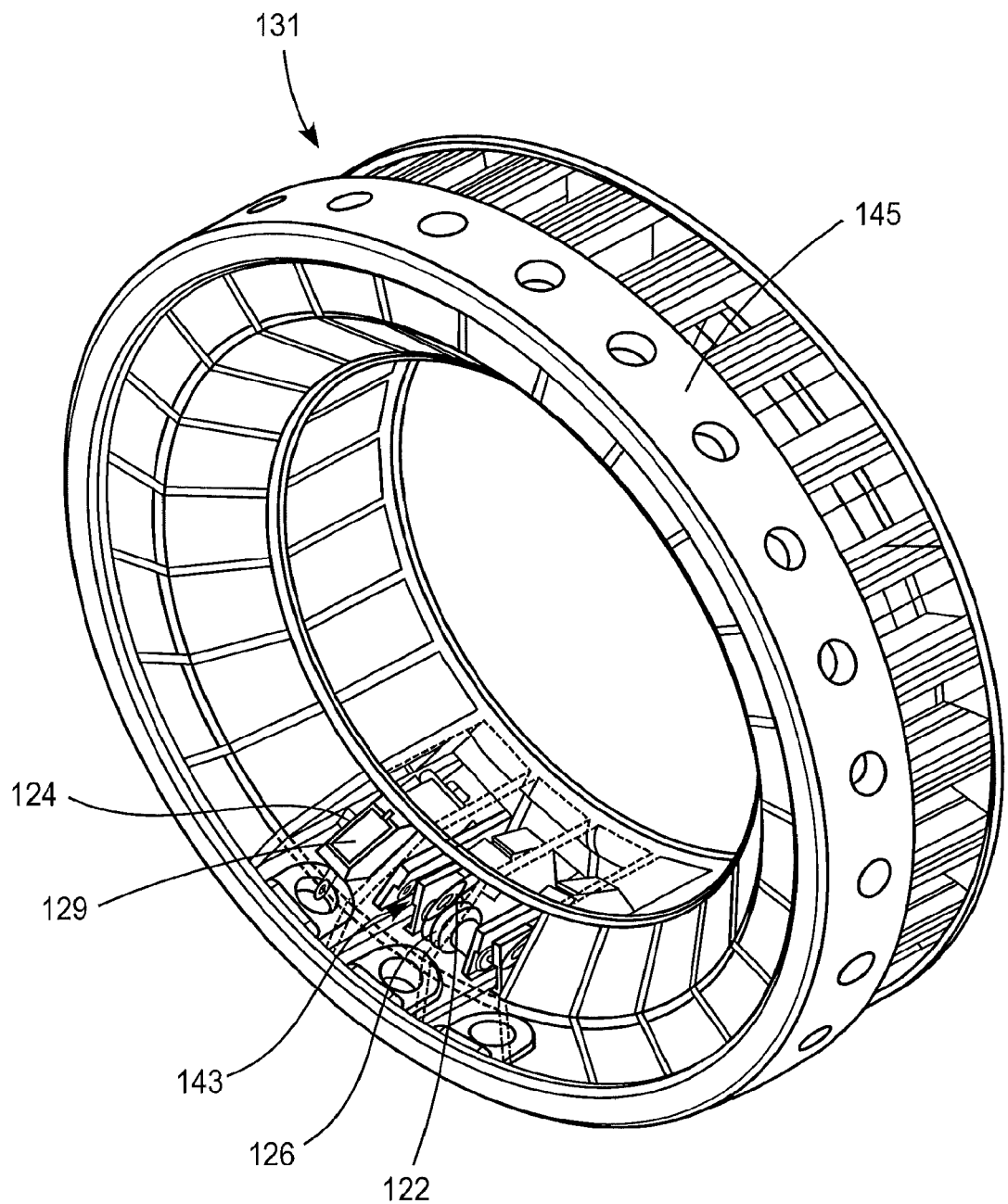
FIG. 8 is a perspective view of a component of the integrated device of FIG. 6.
Figure 9:
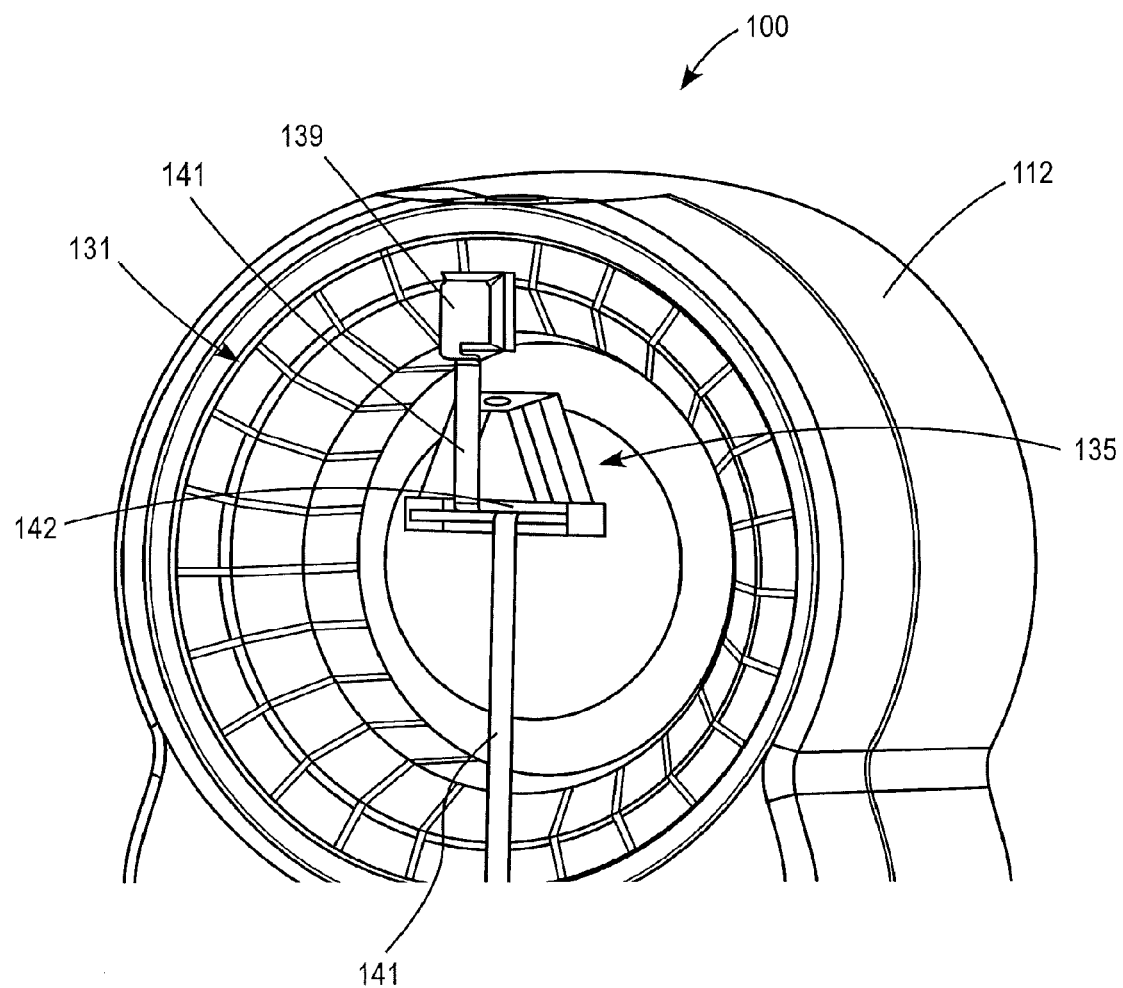
FIG. 9 is a partial perspective view of various components of the integrated device of FIG. 6.

Further details of the optical assembly 135, the light source 139, and the replaceable cartridge 131 are illustrated in FIGS. 8-9. As illustrated therein, the replaceable cartridge 131 generally may comprise a plurality of compartments defining a plurality of body fluid sampling and analysis sites 132. Contained in each sampling and analysis site 132 is a skin penetration member 122. Each skin penetration member 122 can take any suitable form. According to the illustrated embodiment, each skin penetration member 122 is in the form of a hollow needle. It should be understood that alternative skin penetration members may also be utilized consistent with the principles of the present invention (e.g., solid lancets, etc.) each skin-penetration member can be attached to a needle hub 124. Each needle hub 124 is, in turn, attached to an actuation element 126. It should be understood that a number of different actuation elements may be utilized according to the principles of the present invention. The actuation elements can be mechanical, electrical, pneumatic, etc. According to the illustrated embodiment, the actuation element 126 is in the form of a torsional spring and may have those features and characteristics previously described herein. Upon activation, the torsional spring drives the needle hub 124 and the attached skin penetration member 122 into the skin of the user disposed on the footprint 120. According to certain embodiments, each sampling/analysis site 132 further contains a signaling mechanism which produces a detectable signal when contacted with a target analyte contained in a sample of body fluid expressed from the skin. A number of suitable mechanisms are envisioned. The mechanisms may be based on technologies such as photometric or electrochemical analysis. According to the illustrated embodiment, each needle hub 124 contains a reagent pad 129 which generally comprises an absorbent material containing a chemical reagent which, upon reaction with a target analyte, produces a chemical reaction that results in a detectable signal. The reagent pad 129 is in fluid communication with the inner lumen of the skin piercing element 122. As noted above, the signal can be detected optically, electrochemically, or by other suitable means. According to one embodiment, the reagent pad 129, upon reaction with the target analyte, produces a spot which is optically detected by the optical assembly 135 in a manner generally known to those skilled in the art. The spot produced by the above-mentioned reaction can be observed optically through a window 143 formed along the interior region of the illustrated cartridge 131 by the optical assembly 135. In this regard, light emitted from the light source 139 is incident upon the reagent pad 129, and reflects off the surface thereof. Upon formation of a reaction spot on the surface of the reagent pad 129, the amount of light reflected off the reaction spot differs from the light reflected off of other portions of the reagent pad 129 containing no such reaction spot. This reflected light is picked up by the optical assembly, first through the lens 137 (FIG. 7), and eventually is incident upon an optical detector element 142 (FIG. 9).

The optical detector element 142 generally comprises one or more detector elements. According to one alternative construction, the detector element 142 comprises a plurality of detector elements formed in an array. The array can take any suitable configuration, and can be a linear array or an area array according to one nonlimiting example. The detector elements can comprise any suitable construction. For example, the detector elements 142 can comprise a photo diode, CCD, or CMOS based detector element. The signals transmitted to the detector element 142 are passed on to suitable electronics contained within the housing 112 (see, e.g., FIG. 10) via suitable electrical connectors, such as flexible ribbons 141. The specifics of the electronics and signal interpretation being familiar to those of ordinary skill in the art. While not necessary to enable practice of the presently claimed invention, further details concerning the structure, function, and arrangement of the optical assembly 135, and the components contained therein, can be gleaned from the disclosure contained in U.S. Patent Application Publication No. 2006/0281187, entitled ANALYTE DETECTION DEVICES AND METHODS WITH HEMATOCRIT/VOLUME CORRECTION AND FEEDBACK CONTROL, the entire content of which is incorporated herein by reference.

Figure 10:
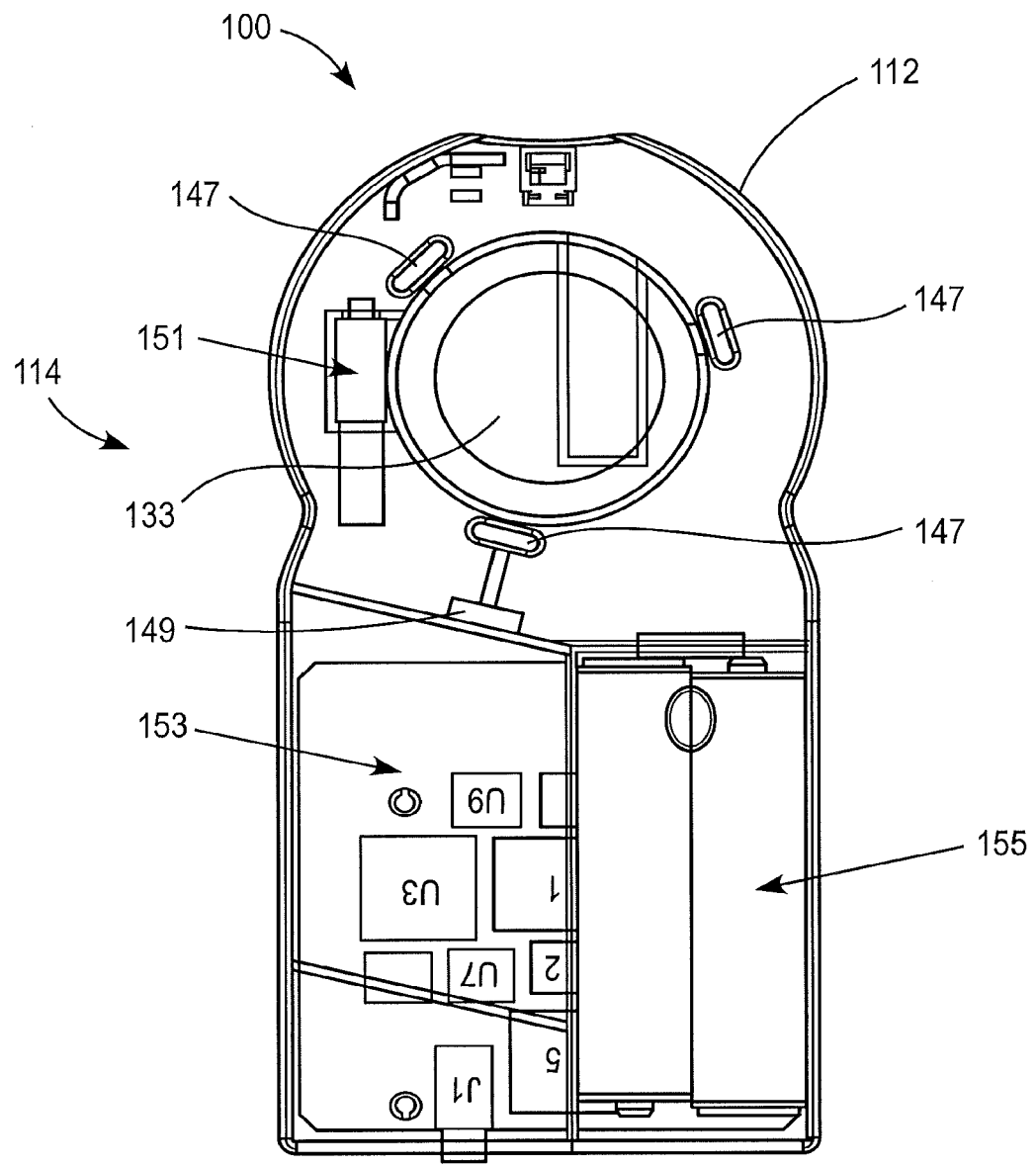
FIG. 10 is a side view illustrating various additional components of the device of FIG. 6.

Additional components of an integrated meter 100 are illustrated in FIG. 10. The view depicted in FIG. 10 is that of an integrated meter 100 with the back panel removed to reveal the above-referenced additional components. For example, as illustrated in FIG. 10, the integrated meter 100 may further include a plurality of rollers 147 which cooperate with the cartridge 131 and a motor drive 149 thereby enabling the rotation of the cartridge 131 about the hub 133, and indexing of the analysis sites 132 with the footprint 120. The integrated meter 100 may also include a catalyst device 114 comprising a pressure pump 151 which, according to certain embodiments, comprises a pump capable of producing at least a negative or vacuum pressure at the surface of the skin located over the footprint 120. The integrated meter 100 may further include appropriate electronics, as embodied in the circuit board 153 of the illustrated embodiment. Preferably, the circuit board contains conventional electronic components capable of controlling the various functions of the integrated meter 100 in the desired manner, including the pump 151. The particulars of the circuit board 153 and electronic components disposed thereon, being well-known to those of ordinary skill in the art. The integrated meter 100 may further comprise a suitable power supply 155, such as the illustrated batteries.

Figure 11:
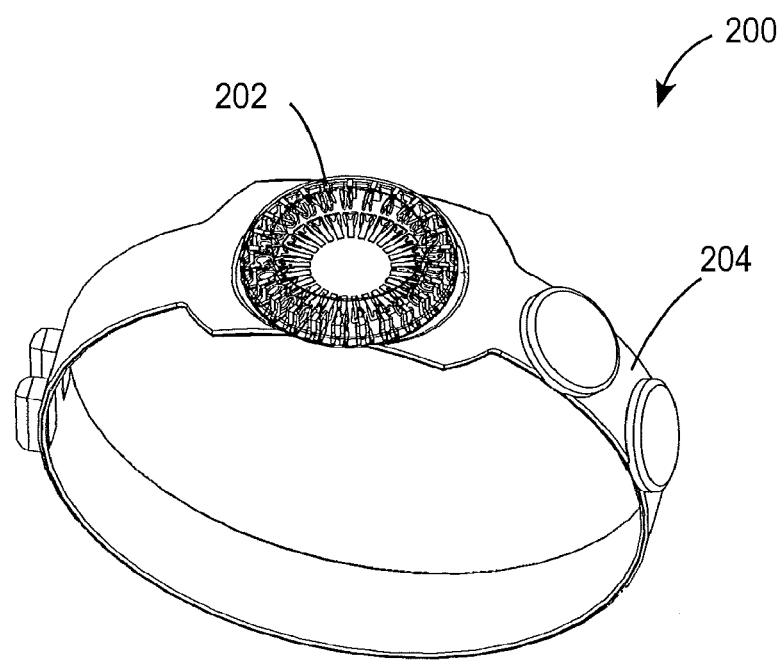
FIG. 11 is a perspective view of an integrated device formed according to an alternative embodiment of the present invention.

As evident from FIGS. 6-10, the integrated meter 100 is configured for handheld use. However, the invention is not limited to handheld devices. For example, the present invention is also directed to integrated meters that are wearable. An example of such a wearable device is illustrated in FIG. 11. The wearable integrated device 200 illustrated therein can be generally composed of a functional portion 202 and a body-attachment portion 204. The functional portion can comprise an arrangement 10 of the type described herein. The functional portion can also have one or more of the features and elements of the handheld integrated meter described above.

According to further aspects of the present invention, modified devices and techniques are provided which permit both digital body fluid sampling and analysis as well as alternate-site body fluid sampling and analysis, which may be performed at the election of the user. In the description that follows, it should be understood that the integrated meters described herein may have any of the features and/or modes of operation than that of the previously described embodiments. For example, the integrated meter that incorporate arrangements of the present invention can include features that facilitate use on digits as well as alternate sites, at the election of the user. Such features are described in U.S. patent application Ser. No. 11/510,784, entitled BODY FLUID MONITORING AND SAMPLING DEVICES AND METHODS, the entire content of which is incorporated herein by reference.

An exemplary body fluid sampling and analysis methodology or technique, which may be utilized in conjunction with any of the above-mentioned catalyst devices or integrated meters, but is not necessarily limited thereto, is described as follows.

A user loads a fresh disposable cartridge containing a plurality of skin penetration members and analysis sites into an integrated meter. The integrated meter then reads calibration data contained in or on the cartridge. This data can be read in any suitable manner. For example, a bar code may be placed on the cartridge which can be optically read by the optical assembly contained within the meter. The integrated meter then selects the proper lookup table or algorithm to calculate an aggregate glucose measurement taking into consideration the calibration data. The meter may then place itself in a ready mode waiting for a trigger to initiate sampling and testing. The user then either manually presses a button or trigger to initiate sampling and analysis, or the device verifies that it is properly positioned on the skin of the user and ready to begin the sampling and analysis procedure. Suitable sensors to accomplish this include optical, capacitive or pressure sensors. The device then initiates a catalyst which acts to facilitate the expression of body fluid. Alternatively, the catalyst is vacuum pressure which generates suction at the sampling site. Optional sensors present in the meter may be used to monitor and control the positive or negative pressure of the catalyst. After achieving a target pressure for a desired period of time, the skin penetration member (e.g., a hollow needle) is actuated and driven into the skin of the user to create a wound site. The skin penetration member comes to rest in or directly on the wound opening created at the sampling site where it obstructs the wound opening and is in the desired position for collecting a sample of body fluid expressed from the wound. The integrated meter may further include a mechanism for detecting a whether a sufficient amount of sample has been expressed. Details of such suitable detection techniques are described in detail in U.S. Pat. No. 7,052,652, entitled ANALYTE CONCENTRATION DETECTION DEVICES AND METHODS, the entire content of which is incorporated herein by reference. Once the desired amount of body fluid has been obtained, the catalyst is deactivated. A sample of body fluid is in fluid communication with a device or mechanism which creates a detectable signal upon reaction within analyte present in the sample body fluid. For example, one such suitable mechanism is an absorbent pad containing a chemical reagent which, upon reaction with the analyte produces a reaction spot which can be optically detected. An optical assembly which is in optical communication with the above described signal generating mechanism is utilized to detect the signal created via reaction with the analyte and communicate the signals to supporting electronics contained within the meter. The concentration of a target analyte (e.g., glucose) can then be calculated using these signals as a basis. Additional factors may be considered during these calculations, such as the sample size, levels of other substances contained in the sample (e.g. hematocrit), etc. Such optional calculation techniques are described in further detail in U.S. Patent Application Publication No. 2006/0281187, entitled ANALYTE DETECTION DEVICES AND METHODS WITH HEMATOCRIT/VOLUME CORRECTION AND FEEDBACK CONTROL, the entire content of which is incorporated herein by reference. These calculations quantify the amount of analyte contained in the sample body fluid. This quantity is displayed on a suitable display contained within the meter which can be easily read by the user. The integrated meter then automatically may retract the skin-penetration member and indexes the disposable cartridge to present a fresh unused skin penetration member which will be utilized to perform the next sampling and analysis event.

Example

A prototype was constructed using a torsional Spring actuator and a needle designed to position the needle on or in the wound (i.e., to obstruct the wound opening). A vacuum catalyst was also utilized. Results of an evaluation of this prototype are summarized in the following table.

| Population | Camino Medical | Camino Medical |
| --- | --- | --- |
| Experiment Name | PAMF1 | PAMF2 |
| Actuator | Beam | Torsional |
| Actuator Version | 2.1 | 5.0 (w/ dwell) |
| # of Subjects | 21 | 19 |
| Probability BV>250 nl | 94% | 93% |
| Probability BV>300 nl | 90% | 91% |
| Probability BV>350 nl | 85% | 85% |
| Average BV (nl) | 985 | 1137 |

The table shows two experiments for which the lancet design, footprint design and footprint contact force were identical. Experiment PAMF1 used a cantilevered beam actuator; this actuator did not allow the needle to remain in or on the wound. Experiment PAMF2 used a torsional coil actuator, this actuator caused the needle to dwell the needle in or on the skin. Surprisingly, the performance of the torsional coil was comparable in blood volume (BV) probabilities to the cantilevered beam. Even more surprising was the observation that the torsional coil actually produced a slightly higher average blood volume.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. §112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. An arrangement for producing a sample of body fluid from a wound opening created in a skin surface at a sampling site, the arrangement comprising:
    a cartridge comprising a plurality of compartments and a plurality of sampling sites, wherein each of the sampling sites comprises
        a skin-penetration member having a first end configured to pierce the surface of the skin, and an inner lumen in communication with the first end,
        a torsional spring actuator operatively associated with the skin-penetration member, and
        a needle hub connecting the skin-penetration member and the torsional spring actuator, wherein the needle hub comprises a reagent pad and wherein the torsional spring actuator is configured to drive the skin-penetration member in an arcuate path to form the wound opening; and
    a detector assembly,
    wherein each of the compartments at least partially encloses the skin-penetration member, torsional spring, and needle hub of a respective sampling site of the plurality of sampling sites.

2. The arrangement of claim 1, further comprising at least one catalyst device comprising a device for applying vacuum pressure, positive pressure, heat, vibration or topical drugs to the sampling site.

3. The arrangement of claim 2, wherein the catalyst device comprises a pump, the pump configured and arranged to apply a vacuum to the sampling site.

4. The arrangement of claim 3, further comprising a controller operatively associated with the pump.

5. The arrangement of claim 1, further comprising a housing, and a footprint disposed on the housing to be applied to the sampling site on the skin of a user.

6. The arrangement of claim 5, wherein the footprint has an opening, the opening having a diameter or major dimension of 3-8 mm.

7. The arrangement of claim 5, wherein the footprint comprises an elastomeric seal.

8. The arrangement of claim 1, wherein the detector assembly comprises at least one CMOS-based detector element.

9. The arrangement of claim 8, wherein the detector assembly comprises a linear or area array of CMOS-based detector elements.

10. The arrangement of claim 1, wherein the skin-penetration member comprises a microneedle.

* * * * *